(12) United States Patent
Smith et al.

(10) Patent No.: US 7,371,270 B2
(45) Date of Patent: May 13, 2008

(54) ODOUR ABSORBING FILTERS

(75) Inventors: Rory James Maxwell Smith, Nr Skipton (GB); Paul Bird, Nr Crawley (GB)

(73) Assignee: Welland Medical Limited (GB)

( * ) Notice: Subject to any disclaimer, the term of this patent is extended or adjusted under 35 U.S.C. 154(b) by 278 days.

(21) Appl. No.: 10/997,284

(22) Filed: Nov. 24, 2004

(65) Prior Publication Data

US 2006/0107642 A1  May 25, 2006

(51) Int. Cl.
*B01D 46/00* (2006.01)
*B01D 53/04* (2006.01)
*B32B 27/12* (2006.01)
*B32B 7/12* (2006.01)
*C09D 34/76* (2006.01)
*A61L 91/00* (2006.01)

(52) U.S. Cl. .................. 55/524; 55/316; 55/522; 55/524; 55/527; 95/135; 95/141; 96/135; 96/137; 96/132; 96/134; 428/317.7; 428/317.9

(58) Field of Classification Search .............. 55/524, 55/486, 487, 385.4, DIG. 35; 96/134, 135, 96/154; 95/153, 132, 134, 135, 154; 210/503; 502/416
See application file for complete search history.

(56) References Cited

U.S. PATENT DOCUMENTS 2,365,729 A * 12/1944 Heise et al. ................. 423/558
3,416,293 A * 12/1968 Alexander ................... 95/136
3,825,494 A *  7/1974 Call et al. .................... 210/138
RE29,410 E *  9/1977 Yoshino ................... 427/389.9
4,957,522 A *  9/1990 Brassell ............................ 96/4
5,162,286 A * 11/1992 MacDowall ................ 502/425
5,338,340 A *  8/1994 Kasmark et al. .............. 96/135
5,436,067 A *  7/1995 Hanamoto et al. ........ 428/293.4
5,927,084 A *  7/1999 Fielding ......................... 62/90
5,948,398 A *  9/1999 Hanamoto et al. ......... 424/76.1
6,331,351 B1* 12/2001 Waters et al. ............. 428/317.7

FOREIGN PATENT DOCUMENTS

GB  2072516 A  * 10/1981
GB  2276324 A  *  9/1994

* cited by examiner

*Primary Examiner*—Duane Smith
*Assistant Examiner*—Ives Wu
(74) *Attorney, Agent, or Firm*—Connolly Bove Lodge & Hutz LLP

(57) ABSTRACT

An odor adsorbing or deodorizing filter which comprises a matrix or substrate impregnated with a mixture of particulate chemically modified activated carbon and particulate activated carbon, together with a binder. The filter may be incorporated into an ostomy collection bag, wound dressing, respirator, air conditioning unit or the like.

13 Claims, 3 Drawing Sheets

ODOUR ABSORBING FILTERS

FIELD OF THE INVENTION

Figure 1:
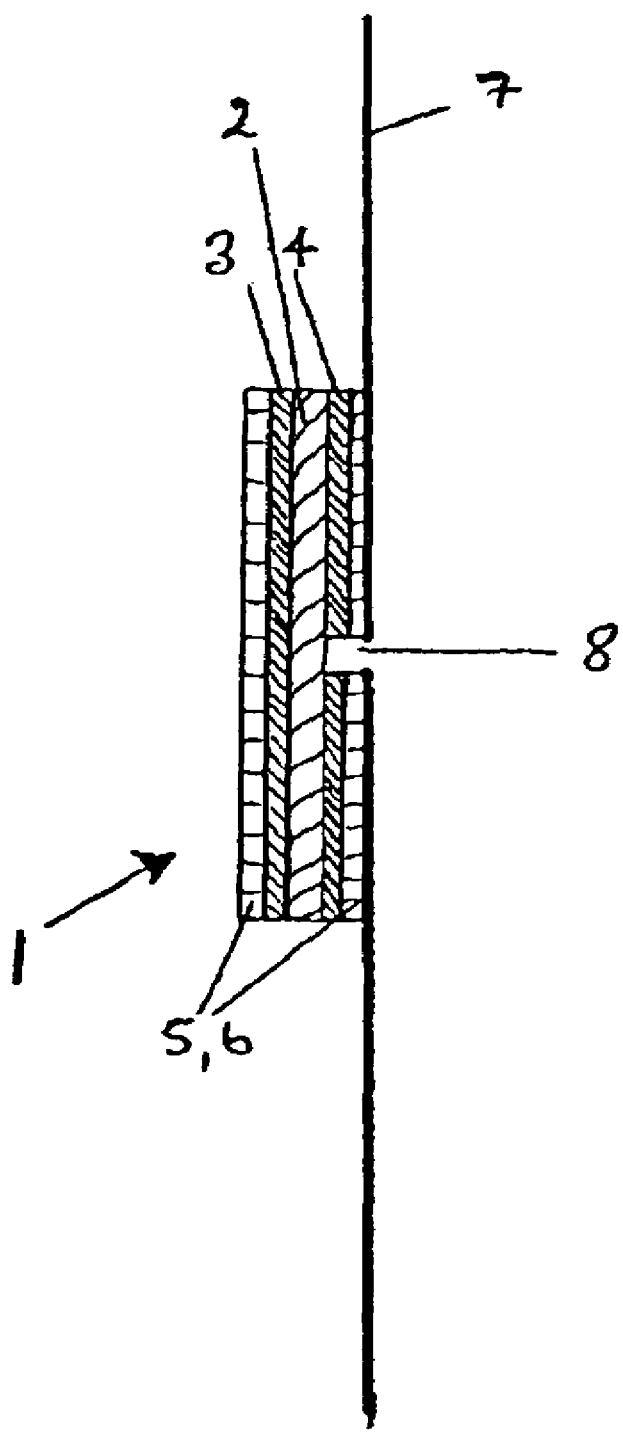

The present invention relates to odour adsorbing or deodorizing filters, in particular to odour adsorbing filters suitable for medical use, for example for incorporation in an ostomy collection bag or in a wound dressing, in order to adsorb the unpleasant odours emanating from an ostomy bag or an infected wound, thereby preventing transmission of such odours.

BACKGROUND OF INVENTION

Ostomy collection bags are discreet pouches or bags which are used to collect the liquid, semi-solid or solid output from a stoma, which is an artificial opening in the abdomen of a patient who has undergone colostomy or ileostomy surgery. A stoma is created in the abdomen wall when a patient has suffered from a bowel obstruction, inflammatory bowel disease, faecal incontinence, trauma, cancer or the like and it enables the bowels to empty.

Ostomy bags can be closed bags that have to be changed 2-3 times a day or alternatively they may be drainable bags that are drained frequently and are then changed every 2-3 days. They contain a filter that allows flatus to be released through a charcoal layer that helps to remove faecal odour.

The composition and odour of faeces varies with diet and moreover the chemistry of the odour emanating from faeces is chemically complex. One cause of faecal odour is due to the presence of a family of sulphur based chemicals known as mercaptans. Other major chemical groups that contribute to the odour are indoles and skatoles, both of which are large cyclic organic compounds.

Filters suitable for use in ostomy bags have been made from microporous activated carbon. The British Standard Test for filter performance challenges the filter with hydrogen sulphide gas. In order to pass and exceed the requirements of the test, chemical treatment of the carbon with, for example, copper, chromium, manganese or iron salts has been necessary. The salt is impregnated and deposited in the microporous activated carbon. Whilst the salt deposited on the surface of the carbon interacts chemically with the hydrogen sulphide and thereby removes it, the impregnating and deposited salt blocks the surface of the carbon with the result that the pores in the body of the structure are much less available to other chemical species for adsorption. Consequently, other odour causing chemicals are not adsorbed so efficiently.

It has now been found that, by selecting a specific mixture of a chemically modified particulate activated carbon and an unmodified particulate activated carbon and impregnating the mixture into a matrix or substrate a filter can be constructed that is very effective in removing the different groups of odour-producing chemicals when the filter is incorporated in an ostomy bag. Alternatively, such a filter can be incorporated into a dressing for application to odour-producing wounds, or into fluid collection devices used to collect infected bodily fluids, such as wound exudates. The filter according to the invention may also be used in respirators, filters used in air conditioning units, for buildings or vehicles as well as for deodorising sewage plants.

SUMMARY OF THE INVENTION

According to the present invention there is provided an odour adsorbing filter suitable for use in medical appliances which comprises a filtration layer formed of a matrix or substrate impregnated with activated carbon together with a binder and sandwiched between cover layers characterised in that the matrix or substrate is impregnated with a mixture comprising from 50 to 95% w/w particulate chemically modified activated carbon and from 5 to 50% w/w particulate activated carbon so that the ratio of chemically modified activated carbon to activated carbon is from 50:50 to 95:5.

According to another aspect of the invention there is provided an ostomy bag incorporating an odour adsorbing filter as defined above.

According to yet another aspect of the present invention there is provided a dressing for a wound said dressing incorporating an odour adsorbing filter as defined above.

DETAILED DESCRIPTION OF THE INVENTION

Preferably the matrix or substrate is impregnated with a mixture comprising from 70 to 87% w/w particulate chemically modified activated carbon and from 13 to 30% w/w particulate activated carbon so that the ratio of chemically modified activated carbon to activated carbon is from 70:30 to 87:13. The mixture may comprise from 70 to 80% w/w particulate chemically modified activated carbon and from 20 to 30% w/w particulate activated carbon so that the ratio of chemically modified activated carbon to activated carbon is from 70:30 to 80:20.

The matrix or substrate is most preferably impregnated with a mixture comprising of 75% w/w particulate chemically modified activated carbon and 25% w/w particulate activated carbon.

Alternatively the matrix may be impregnated with a mixture of particulate chemically modified activated carbon and particulate activated carbon where the ratio is from 55:45 to 90:10, preferably from 60:40 to 85:15, most preferably 65:35.

The matrix or substrate that is impregnated with the mixture of activated carbons according to the invention may be a fabric, such as a non-woven fabric, e.g. felt, or a knitted fabric. Alternatively, the matrix may be a foam, for example a polyurethane foam or any other open cell or reticulated foam, or paper. When the deodorizing filter is to be used in a wound dressing the matrix may be a textile fabric or a foam.

The chemically modified particulate activated carbon is prepared by impregnating a starting material, which may be wood, coconut shell or fabric, with a salt of copper, chromium, manganese or iron, or organic material such as tetra ethylenediamine before being carbonised in a furnace. The preferred salt is copper nitrate. The starting material is impregnated with from 9 to 15% (w/w), preferably from 11 to 13% (w/w), most preferably 12% (w/w) measured as copper oxide using atomic absorption spectroscopy.

Following carbonisation the treated carbon is activated using steam at high pressure. Activation usually takes place at 800 to 1000° C. under strictly controlled atmospheric conditions and in the presence of $CO_2$ and water vapour.

Following activation the carbon is ground, for instance using a ball mill, to reduce the particle size such that 0% remains on a sieve of 40 micron mesh size and 80% will pass through a sieve having a mesh size of 32.5 micron.

The untreated particulate activated carbon component of the filtration layer is prepared by the same method but without the impregnation step.

In order to make the filter of the invention, the selected mixture of carbons i.e. particulate chemically modified activated carbon and the particulate activated carbon are weighed into a rotary mixing machine, which is allowed to operate until complete and intimate mixing is achieved. This usually takes in the order of 30 minutes.

The desired matrix or substrate, which may be a felt type non-woven fabric, is passed over a conveyor. The intimate mixture of particulate carbons is applied from above and drawn into the body of the matrix by the application of a vacuum to the underside of the conveyor, using the process as described in U.S. Pat. No. 5,281,437.

In order to stabilise the composite structure of matrix impregnated with the activated carbon mixture the retained particulate carbon is fixed with a binder. The binder may be applied to the impregnated matrix by means of an applicator roller that receives the binder solution or suspension from a reservoir via a spreader that spreads binder over the surface of the applicator roller. From 10% to 25% w/w of binder may be applied to the impregnated matrix, preferably from 15% to 19% w/w.

Binders for use in the present invention may be selected from natural or synthetic latexes, for example styrene butadiene, acrylonitrile butadiene, acrylic methyl methacrylate polyvinyl alcohol, polyvinyl acetate, melamineformaldehyde resins or they may comprise solutions of starch, carboxymethyl cellulose, methyl cellulose or sodium silicate. The preferred binder is an acrylonitrile binder.

Following the application of the binder a net-like thermofusible layer, which may be made from polyurethane, polyethylene, ethyl vinylacetate, nylon or similar low melting point materials, is applied to each surface of the impregnated matrix using a belt laminator to form a composite structure.

A film of relatively fluid impervious material is then laminated to each surface of the composite structure to provide fluid impervious cover layers. The film of fluid impervious material comprises ethyl vinylacetate, polyvinylchloride, polyurethane, polyethylene, etc. The preferred film consists of a co-extruded film of ethyl vinyl acetate, polyvinyl dichloride and ethyl vinyl acetate known as Cryovac (Registered Trade Mark).

The resulting multi-layer composite is cut into discs, preferably about 25 mm in diameter, using a rotary or flat bed press.

An odour adsorbing filter in accordance with the invention will now be described by way of reference to the accompanying drawing (FIG. 1) which is a section through a filter attached to the wall of an ostomy bag.

The filter 1 consists of a filtration layer 2 composed of a felt matrix impregnated with a mixture of 75% particulate chemically modified activated carbon (containing 12% as copper oxide) and 25% particulate activated carbon. The matrix formed is then treated with up to 19% w/w acrylonitrile binder. The filtration layer 2 is sandwiched between two layers, 3 and 4, of a net-like thermofusible web composed of ethyl vinyl acetate. Laminated on the outer surface of each of the thermofusible layers 3 and 4 is a 75 micron co-extruded film, 5 and 6, composed of ethyl vinyl acetate/polyvinyl dichloride/ethyl vinyl acetate.

The filter 1 which is in the form of a disc having a diameter of 25 mm is positioned on the inside of one wall 7 of an ostomy bag. The wall 7 of the ostomy bag is composed of a film of ethyl vinyl acetate/polyvinyl dichloride/ethyl vinyl acetate. In order to attach the filter 1 to the wall 7, heat is applied using a welding tool. Combined with the welding tool is a knife-edge that is positioned centrally so as to punch a hole through the bag wall 7 and through one of the co-extruded film layers 6. Thus gas can flow into the filtration layer 2 of the filter 1 around the perimeter and out of the centre of the filter 1 via a hole 8.

EXAMPLE 1

Testing of Deodorising Capability of Filters

Purpose of Evaluation:

Principally, to assess the chemisorption and physisorption properties of the filter materials supplied for the study.

Also, to compare the filters with a standard sample from "Charcoal Cloth" and with a Dansac sample.

Samples

Filters "40" 0% chemically modified carbon: 100% unmodified carbon

Filters "41" 25% chemically modified carbon: 75% unmodified carbon

Filters "42" 50% chemically modified carbon: 50% unmodified carbon

Filters "43" 75% chemically modified carbon: 25% unmodified carbon

Filters "44" 100% chemically modified carbon: 0% unmodified carbon

Charcoal Cloth "01"

Dansac Pouches

The particulate chemically modified carbon was prepared by impregnating wood with 12% w/w copper nitrate, which was then carbonised. Following carbonisation the treated carbon was activated at 875° C. with steam at a pressure of 1 bar. The carbon so produced was then ground in a ball mill to reduce the particle size so that 80% passed through a sieve having a mesh size of 32.5 micron.

The activated carbon was prepared in a similar manner, but without the addition of copper nitrate.

The test filters were prepared by impregnating a felt matrix with a mixture of particulate chemically modified activated carbon and particulate activated carbon. The matrix thus formed was treated with 19% w/w acrylonitrile binder, following which it was sandwiched between two layers of thermofusible web composed of ethyl vinyl acetate.

The Charcoal Cloth International Ltd filters and The Dansac Pouch filter comprise 100% activated carbon impregnated with salts reactive to hydrogen sulphide but differ in construction.

All of the filter samples were supplied as 25 mm discs welded to a sheet of film. Into one side was punched a 3 mm slit to enable the gas to pass through the filters. The filters were designed such that gas flowed in through the exposed sides of the filter and out through the central slit.

The filters on the Dansac pouch were squares of 20 mm×20 mm, and were cut out of the pouch to be tested in the same manner as the other filters. The gas exit path on the Dansac filters was noted to be circular with a diameter of between 4 mm-5 mm.

Test Methods:

Physisorption Testing

Physisorption capacity testing at 500 ml/min. GC grade Nitrogen containing 288±32 ppm of menthol.

The filter is deemed to have failed when 32 ppm menthol passes through the filter (equivalent to detecting 50 ng per 50 µl sample injection).

See Appendix for more information relating to the physisorption testing of the filters.

Chemisorption Testing $H_2S$ deodorising capability at 250 ml/min flow rate. A mixture of nitrogen (80%) and methane (20%) with 25±2 ppm $H_2S$.

Filters which are designed to use a radial gas flow path (as in this case) are normally tested at 500 ml/minute in order to reduce the length of time required to test the filters. However, these samples were all tested at 250 ml/min. The test ends and the filter is deemed to have failed when 2 ppm of $H_2S$ passes through the filter.

Results:

Physisorption Test Results: Minutes to Reach 2 ng/50 µl sample:

TABLE 1

| Sample Type | Sample 1 | Sample 2 | Sample 3 |
| --- | --- | --- | --- |
| 40 | 107 | 116 | 122 |
| 41 | 102 | 100 | — |
| 42 | 82 | 82 | 86 |
| 43 | 82 | 68 | 64 |
| 44 | 80 | 64 | 90 |
| 01 | 14 | 14 | — |
| Dansac | 70 | 89 | 84 |

Figure 2:
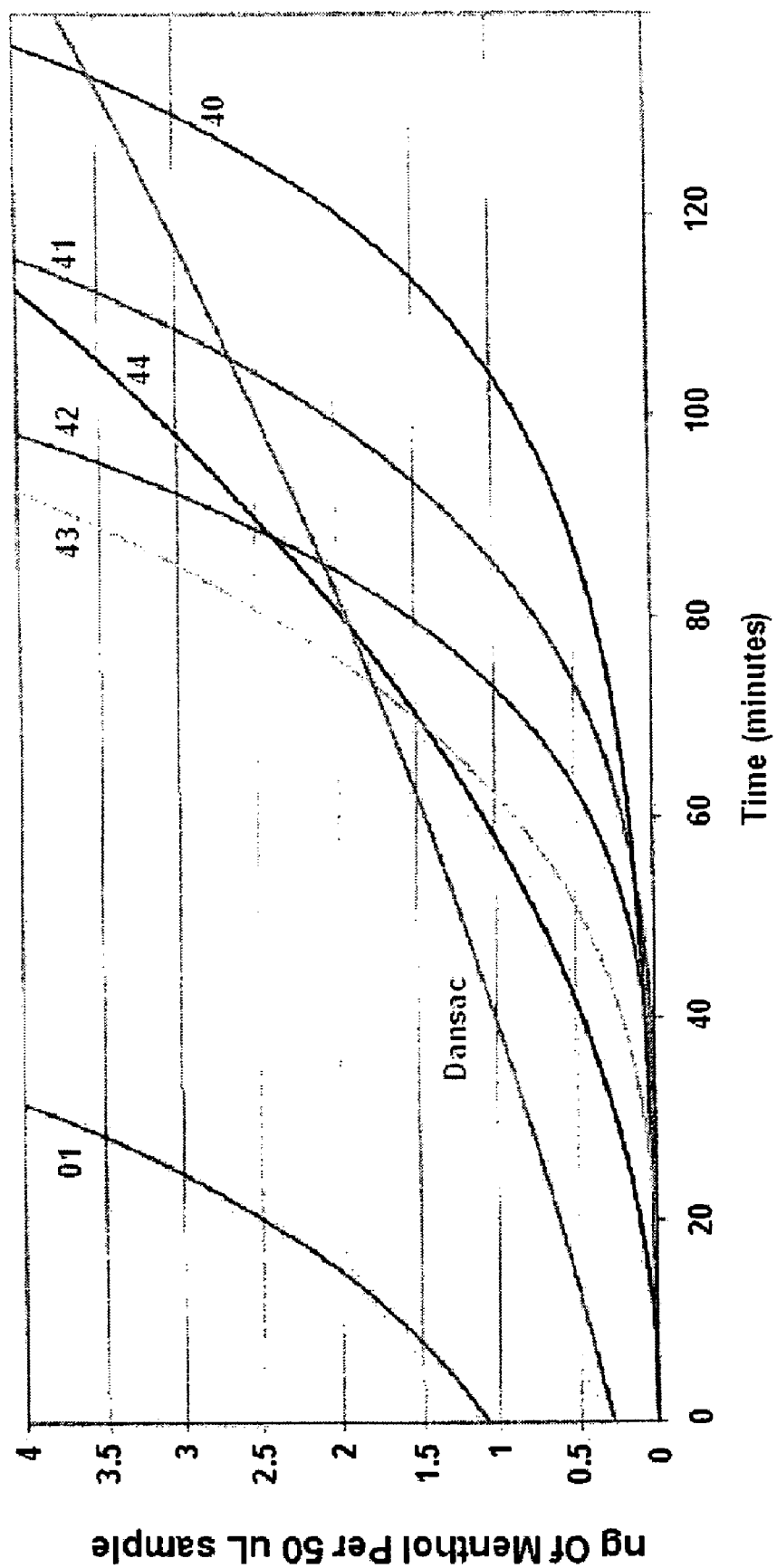

The raw data was averaged and plotted onto a graph: see FIG. 2.

From the graph in FIG. 2 it can clearly be seen that the worst performing filter is the standard charcoal cloth sample, since it immediately allowed a high concentration of menthol through. The Dansac filter also allowed some menthol to pass and the level rose gradually. All of the test samples "40" to "44" were considered to have performed better than either "01" (the standard charcoal cloth) or the Dansac filter. Of all the samples tested, there was a clear trend in the performance:

40>41>42>43>44

It should be noted that, although 2 ng/50 µl sample is chosen as the failure point, many organic odours would most likely be detectable to the human nose at lower levels, hence the failure profile shown by the Dansac filters is considered to be much worse than that of (for example) "42" since the Dansac filter allowed some menthol to pass right from the beginning of the test. "42" allowed no odour to pass until beginning to fail sharply after 40 minutes.

Chemisorption Test Results

Hydrogen Sulphide Testing: Minutes to 2 ppm $H_2S$:

TABLE 2

| Sample Type | Sample 1 | Sample 2 | Sample 3 |
| --- | --- | --- | --- |
| 40 | 3 | 1 | 3 |
| 41 | 24 | 18 | 21 |
| 42 | 24 | 27 | 20 |
| 43 | 66 | 54 | 56 |
| 44 | 104 | 83 | 104 |
| 01 | 27 | 22 | 8 |
| Dansac | 227 | 272 | 227 |

Figure 3:
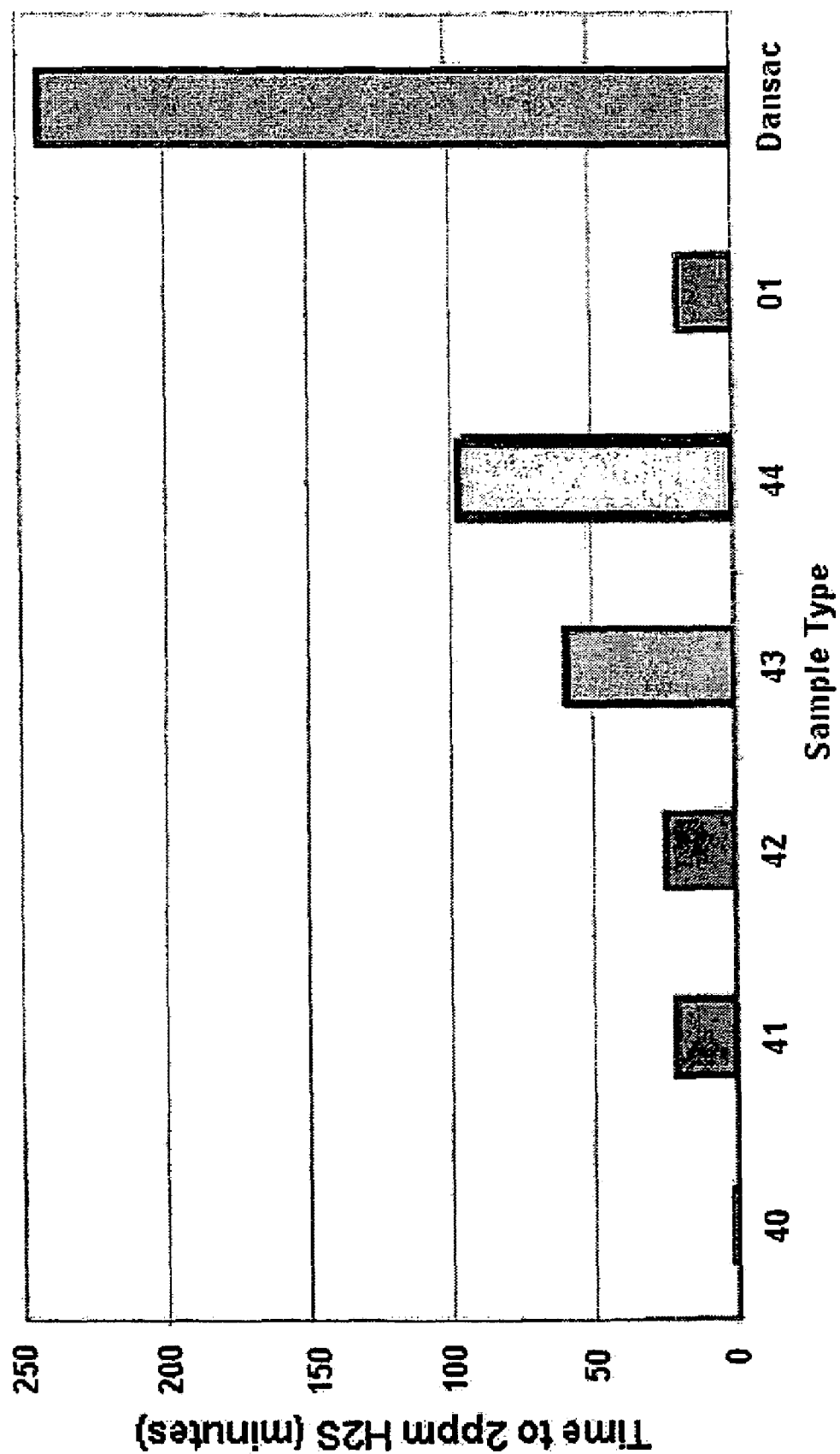

The average results were plotted onto a graph: see FIG. 3.

The graph in FIG. 3 clearly shows that the Dansac filter performed better than any other sample, and that the "01" filter again performed badly.

This, taken along with the physisorption results, suggests that the Dansac filter consists entirely of carbon activated to adsorb $H_2S$.

Interestingly, the "40" to "44" filters were ranked in the opposite order to the physisorption testing, thus:

44>43>42>41>40 this is not surprising considering the different loadings of the filters, and the results can be summarised as follows:

TABLE 3

| Sample Type | Chemisorption Rank | Physisorption Rank |
| --- | --- | --- |
| 40 | 5th | 1st |
| 41 | 4th | 2nd |
| 42 | 3rd | 3rd |
| 43 | 2nd | 4th |
| 44 | 1st | 5th |

Conclusions:

It was possible to find a clear trend in the performance of the different types of filter in the physisorption and chemisorption tests.

The standard Charcoal Cloth filter "01" was found to perform very poorly in every test.

The Dansac filter out-performed all of the other filter types in the chemisorption test, but was poor in physisorption tests. It is probably composed only of carbon which has been activated specifically to adsorb $H_2S$.

Whilst the Dansac filter appeared to be the best at adsorbing hydrogen sulphide, its performance in the physiosorption test, a test model for the adsorption of other odiferous molecules, was worse than any of the test filters. The test filters, in particular filters "42" and "43", showed that they would adsorb both $H_2S$ and other odiferous molecules well Appendix Justification for the Use of Menthol as a Suitable Physisorption Test Material:

Ideally, the physisorption test should consist of materials which the filter will be required to remove in real-life use. Such substances would for example be indole, skatole or other organic compounds produced by the human digestive system.

So far, it has not been possible to devise a suitable test method which uses such materials due to problems with low vapour pressures (which mean that each filter test run can last for many hours) and equipment contamination (which makes accurate run-run reproducibility impossible).

It was therefore decided to use a substance similar in molecular weight and structure to some of these compounds but which was more suited to the test procedure. It is also important that the substance be removed from the gas stream by physisorption alone, i.e. it does not interact with the chemisorption-activated carbon. Menthol satisfies these criteria:

TABLE 5

| Material | Molecular wt |
| --- | --- |
| Menthol | 156 |
| Indole | 117 |
| Skatole | 131 |

All these materials are based around a reasonably rigid 6-carbon skeleton, and can be expected to have similar affinities for activated carbon.

The extra ingredients in the carbon are specific to $H_2S$ removal, for example:

$CuO + H_2S \rightarrow CuS + H_2O$

Depending on the active substance, water is often released during the reaction with $H_2S$. Menthol does not react in this way.

It is also apparent from the results that $H_2S$ and menthol are removed by different mechanisms. $H_2S$-removing carbon will generally adsorb some menthol since the gas will still be attracted to the carbon (e.g. sample "44", above, with 100% $H_2S$ activated with for example: metal compounds (e.g. "40", with no $H_2S$-activated carbon).

EXAMPLE 2

Patient Trial of Filter

Odour and security of a stoma appliance are two of the most major concerns for a patient following formation of a colostomy. Research from as far back as 1985 states these two concerns to be ranked in the top three concerns for a patient.

The objective of the trial was to show that the new filter in accordance with the invention was more effective in dealing with the two very different types of odour that faeces produce when compared to the users usual pouch.

Trialists

A simple tick box questionnaire was sent to thirty 'ostomists'. To date, twenty have responded.

All colostomists were given five of each type of pouch to use.

Other appliances used included Convatec, Dansac, Braun and Coloplast.

All trialists have all had their colostomies for varying periods of time, i.e. one to eight years and were competent in the management of their stomas.

Two different filters were tested. The new filter is designed to deal with the two very different types of odour that faeces produces. These being in origin, cyclic organics that are dealt with by pores in the carbon of the filter and the sulphurous chemicals eliminated by the chemically activated part of the filter.

The trial involved ostomists trying two different filters. The filters had varying ratios of chemically modified and unmodified activated carbon within them.

Filter "A" consisted of a 50/50 blend of modified and unmodified carbon, whilst Filter "B" consisted of 75/25 blend of modified and unmodified carbon.

Results of the Questionnaire

The Filter

When Trialling the New Filter

19/20 90% people found the filter on pouch B better or equivalent to that of their usual pouch;

15/20 trialists found filter B better; and

4/20 trialists found filter B equivalent to their usual pouch.

EXAMPLE 3

Patient Questionnaire

A simple tick box questionnaire was sent to users of colostomy bags containing the new "Dual Carb" filter, which consisted of a 75/25 blend of modified and unmodified carbon.

Results

All the 103 people who returned their questionnaires responded positively to the question "Was the Dual Carb filter effective in odour control?"

The people who returned their questionnaire had previously been using the following brands of colostomy pouches:—

| | |
|---|---|
| Welland old style (pre-Dual Carb) | 45 |
| Coloplast | 19 |
| Convatec | 11 |
| Pelican | 3 |
| Dansac | 13 |
| Hollister | 6 |
| Braun | 5 |
| Simcare | 1 |

The Following Unsolicited Comments were Received:—

"The filter was a great improvement".

"The best yet".

"No pancaking and less odour".

"This new filter is much better than the one I use at present".

"Very effective odour control".

"I thought the (odour) filtration was much better".

The invention claimed is:

1. An odour absorbing filter for use in medical appliances comprising a filtration layer formed of a matrix or substrate impregnated with activated carbon together with a binder and sandwiched between cover layers characterized in that the matrix is impregnated with a mixture comprising from 70 to 87% w/w particulate chemically modified activated carbon and from 13 to 30% w/w particulate activated carbon so that the ratio of chemically modified activated carbon to activated carbon is from 70:30 to 87:13.

2. The filter according to claim 1, wherein the matrix is impregnated with a mixture comprising from 70 to 80% w/w particulate chemically modified activated carbon and from 20 to 30% w/w particulate activated carbon so that the ratio of chemically modified activated carbon to activated carbon is from 70:30 to 80:20.

3. The filter according to claim 1, wherein the matrix is impregnated with a mixture comprising 75% w/w particulate chemically modified activated carbon and 25% w/w particulate activated carbon.

4. The filter according to claim 1, wherein the matrix or substrate is selected from non-woven, woven or knitted fabric or a foam.

5. The filter according to claim 1, wherein the chemically modified activated carbon is obtainable by impregnating a starting material with copper nitrate.

6. The filter according to claim 4, wherein the starting material is impregnated with from 9 to 15% w/w measured as copper oxide using atomic absorption spectroscopy.

7. The filter according to claim 4 or claim 5, wherein the starting material is 30 selected from wood, coconut shell or fabric.

8. An ostomy bag incorporating an odour absorbing filter according to any one of claims 1 to 6.

9. A wound dressing incorporating an odour absorbing filter according to any one of claims 1 to 6.

10. A fluid collection device for collecting bodily fluids incorporating an odour absorbing filter according to any one of claims 1 to 6.

11. A respirator incorporating an odour absorbing filter according to any one of claims 1 to 6.

12. An air conditioning unit incorporating an odour absorbing filter according to any one of claims 1 to 6.

13. A sewage plant incorporating an odour absorbing filter according to any one of claims 1 to 6.

* * * * *